United States Patent
Preuss et al.

(10) Patent No.: US 9,820,854 B2
(45) Date of Patent: Nov. 21, 2017

(54) INCREASING THE BREAKING LOAD OF CERAMIC CUP INSERTS FOR HIP JOINT PROSTHESES BY A DEFINED BACK SIDE COLLISION OF THE CUP INSERT AND ACETABULAR CUP

(75) Inventors: Roman Preuss, Kirchheim Unter Teck (DE); Thomas Pandorf, Wenau (DE)

(73) Assignee: CeramTec GmbH, Plochingen (DE)

( * ) Notice: Subject to any disclaimer, the term of this patent is extended or adjusted under 35 U.S.C. 154(b) by 0 days.

(21) Appl. No.: 13/642,745

(22) PCT Filed: Apr. 29, 2011

(86) PCT No.: PCT/EP2011/056838
§ 371 (c)(1),
(2), (4) Date: Oct. 22, 2012

(87) PCT Pub. No.: WO2011/135074
PCT Pub. Date: Nov. 3, 2011

(65) Prior Publication Data
US 2013/0046388 A1    Feb. 21, 2013

(30) Foreign Application Priority Data

Apr. 30, 2010   (DE) .................. 10 2010 028 402
Jul. 16, 2010   (DE) .................. 10 2010 031 438

(51) Int. Cl.
*A61F 2/32*     (2006.01)
*A61F 2/34*     (2006.01)
*A61F 2/30*     (2006.01)

(52) U.S. Cl.
CPC ...... *A61F 2/34* (2013.01); *A61F 2002/30332* (2013.01); *A61F 2002/30563* (2013.01);
(Continued)

(58) Field of Classification Search
CPC ............... A61F 2/34; A61F 2002/3438; A61F 2002/30332; A61F 2310/00023; A61F 2310/00179
(Continued)

(56) References Cited

U.S. PATENT DOCUMENTS 5,824,107 A * 10/1998 Tschirren ............... 623/22.28
5,879,397 A    3/1999 Kalberer et al.
(Continued)

FOREIGN PATENT DOCUMENTS

DE    196 54 409 C1    4/1998
DE    198 13 074 A1    9/1999
(Continued)

*Primary Examiner* — Brian Dukert
(74) *Attorney, Agent, or Firm* — Norton Rose Fulbright US LLP

(57) ABSTRACT

The invention relates to an acetabular cup (4) and a cup insert (3) for a hip joint prosthesis (12), wherein the cup insert (3) is coupled to the acetabular cup by means of a clamping cone (5) of a conical clamping device in the equatorial region (7) of the two components (3, 4) and, in the unloaded state of the cup insert (3), a gap (8) is provided between the two components (3, 4) below the clamping cone (5) to the pole (6), said gap being delimited by the radial contours of the two components (3, 4). In order to reduce the tensile stresses in the cup insert, the radial contours of the two components (3, 4) have identical geometric elements in the same order, starling front the lower cone end (9) to the pole (6), and tangential or substantially tangential transitions exist between the geometric elements.

7 Claims, 2 Drawing Sheets

(52) U.S. Cl.
CPC .......... *A61F 2002/3412* (2013.01); *A61F 2002/3438* (2013.01); *A61F 2310/00011* (2013.01); *A61F 2310/00203* (2013.01); *A61F 2310/00239* (2013.01); *A61F 2310/00317* (2013.01)

(58) Field of Classification Search
USPC .......... 623/17.14, 22.14, 22.15, 22.17–22.2, 623/22.21–22.39, 23.4, 23.41, 23.43
See application file for complete search history.

(56) References Cited

U.S. PATENT DOCUMENTS

| | | | |
|---|---|---|---|
| 5,919,236 | A | 7/1999 | Pfaff et al. |
| 6,797,007 | B1 | 9/2004 | Von Chamier et al. |
| 7,393,362 | B2 | 7/2008 | Cruchet et al. |
| 8,226,728 | B2 | 7/2012 | Preuss et al. |
| 8,419,800 | B2 * | 4/2013 | Tuke et al. .............. 623/22.21 |
| 2005/0033442 | A1 * | 2/2005 | Fisher et al. ............. 623/18.11 |

FOREIGN PATENT DOCUMENTS

| | | |
|---|---|---|
| EP | 0 649 641 A2 | 4/1995 |
| EP | 0 796 598 A2 | 9/1997 |
| EP | 0 826 347 A1 | 3/1998 |
| EP | 1 025 814 A1 | 8/2000 |
| EP | 1 066 806 A1 | 1/2001 |
| EP | 1 442 727 A2 | 8/2004 |
| WO | 2008/015286 A2 | 2/2008 |

* cited by examiner

INCREASING THE BREAKING LOAD OF CERAMIC CUP INSERTS FOR HIP JOINT PROSTHESES BY A DEFINED BACK SIDE COLLISION OF THE CUP INSERT AND ACETABULAR CUP

This application is a §371 of International Application No. PCT/EP2011/056838 filed Apr. 29, 2011, and claims priority from German Patent Application Nos. 10 2010 028 402.5 filed Apr. 30, 2010 and 10 2010 031 438.2 filed Jul. 16, 2010.

FIELD OF THE INVENTION

The invention relates to a hip socket and a socket insert for a hip joint prosthesis, wherein the socket insert is coupled to the hip socket by means of a damping cone of a conical damping connection in the equatorial region of the two components, and beneath the damping cone a gap is situated between the two components up to the pole, the gap being delimited by the radial contours of the two components.

Background Of The Invention

Various materials are used for achieving a biocompatible, low-wear bearing for modern hip joint prostheses. The so-called hard-hard pairings according to the prior art are best suited for long-term reliable care of the patient. In these pairings, the bail head mounted on the hip stem as well as the socket insert mounted in the hip socket are made of a hard material in the technical sense. Ceramic-ceramic and metal-metal pairings are presently in use. Current studies are also investigating the clinical effects of the ceramic-metal pairing.

To provide the surgeon with the opportunity to intra-operatively select the optimal slide pairing for the patient, modern hip joint prostheses have a modular design (see FIG. 1). The implants are generally composed of a shank 1 which is coupled to a ball head 2, and a hip socket 4 which is coupled to a socket insert 3. The shank and the hip socket are generally made of metal alloys, and are joined to the body by ingrowth into the femur and the pelvic bone, respectively. The shank and the hip socket are supports for the ball head and the socket insert, respectively. The ball head is rotatably supported in the spherical recess of the socket insert with a degree of freedom of one.

The coupling between the socket insert and the hip socket is achieved with a direct coupling without the insertion of an adapter material such as plastic, and as a rule, by means of a conical clamping connection. Approaches in this regard are described in EP 0 649 641, EP 0 826 347, and DE 196 54 409, for example. The components are usually coupled by a clamping cone situated in the so-called equatorial region of the hip socket. For an illustration of the term "equatorial," see FIG. 2, reference numeral 5. There is no contact in the so-called polar region of the components; instead, a significant gap is provided to avoid contact of the components in this region (see EP 0 649 641, FIG. 1, and EP 0 826 347, FIGS. 1 through 4). For an illustration of the term "polar," see FIG. 2, reference numeral 6.

The need for avoiding contact of the components in the back-side region of the socket insert (the geometric area beneath the clamping cone up to the pole) is based on the following:

1. Load on the socket insert causes slight load-dependent sinking of the socket insert into the hip socket. If contact occurs prematurely between the components in the back-side region, this results in relief of load on the clamping cone. As a result, the clamping force of the coupling does not further increase, but, rather, remains at the lowest possible level. If tensile forces are then transmitted to the socket insert due to adhesion between the ball head and the socket insert, the socket insert may be lifted from the hip socket.

This malfunction of the coupling may ultimately lead to failure of the prosthetic system in vivo.

On the other hand, if there is a sufficient gap between the components, the clamping force increases unhindered with increasing load on the socket insert, thus ensuring adequate clamping of the components.

2. If contact between the components occurs in the back-side region, it must be ensured that the contact takes place not at specific points, but, rather, over the surface area. Point contact results in localized increases in stress which lead to overload and premature failure. However, surface contact cannot be ensured for the indicated geometries.

Minor geometric deviations, which are always possible within the scope of allowable tolerances, as well as slight tilting in the hip socket due to asymmetrical loads, etc., result in point contacts, and thus, premature failure. Some studies have shown that a controlled surface contact in the back-side region is not possible with the present geometries.

It is assumed that a controlled back-side contact of the components, while avoiding or solving the described problems, results in a reduction in the tensile stresses in the socket insert, which has a positive effect in particular when ceramic socket inserts are used. The breaking load of the socket inserts would thus be significantly increased. When socket inserts made of metal alloy are used, it is expected that the reduction in the stresses results in less deformation. This may result in a reduction in the load-induced shape deviation of the sliding surfaces and a decrease in the wear of the sliding partners.

Some studies emphasize the need for the back-side gap between components having this or a similar geometry.

OBJECT AND SUMMARY OF THE INVENTION

The object of the invention is to improve a hip socket and a socket insert for a hip joint prosthesis in such a way that a reduction in the tensile stresses in the socket insert is achieved.

According to the invention, this object is achieved by the features udescribed herein.

As a result of the radial contours of the two components having identical geometric elements in the same sequence, starting from the lower cone end to the pole, and tangential or substantially tangential transitions occurring between the geometric elements, a reduction in the tensile stresses in the socket insert is achieved.

DETAILED DESCRIPTION

Figure 1:
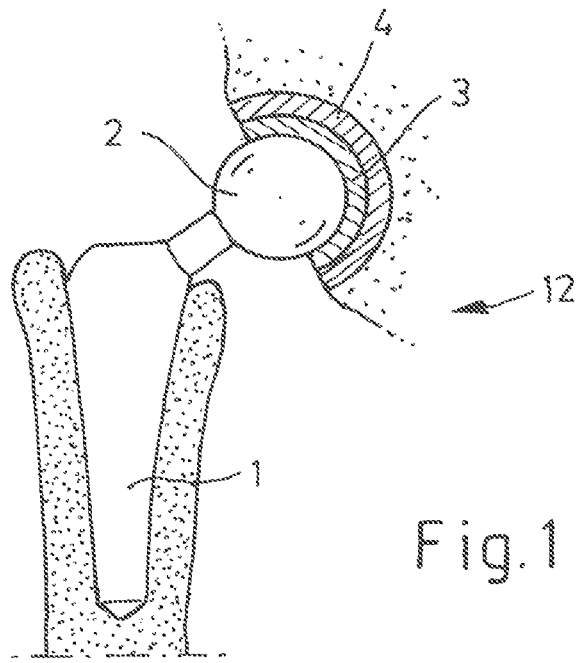
FIG. 1 is hip joint prostheses have a modular design according to the prior art.

In one preferred embodiment, the gap is an initial gap which is largest in the unloaded state of the socket insert, and which decreases when load is applied to the socket insert, and which is at least partially closed above a certain load, so that contact of the components also occurs beneath the clamping cone. The breaking load of the socket insert is thus significantly increased by a controlled backside contact.

The width of the initial gap between the components in the unloaded state of the socket insert in the region near the cone is preferably less than or equal to the width of the gap in the region of the pole.

Alternatively, the width of the initial gap between the components in the unloaded state of the socket insert continuously increases, starting from the region near the cone to the pole.

The hip socket is preferably made of metal and has thin walls, and thus has a particularly flexible design. As a result, when load is applied to the socket insert the hip socket may expand, and the socket insert on the clamping cone may slide into the interior of the hip socket until, above a certain load, contact of the components also occurs beneath the clamping cone.

The socket insert is advantageously made of ceramic, and is preferably made of an aluminum oxide ceramic or mixed ceramics based on aluminum oxide or zirconium oxide, or a silicon-nitride ceramic.

In one embodiment of the invention, the back side of the socket insert, exactly the same as the internal geometry of the hip socket, has the design of a portion of a ball sphere.

In one embodiment, except for on the clamping cone, the radius $R_{insert\ back\ side}$ ($R_{ER}$) of the back side of the socket insert is greater than or equal to the radius $R_{socket\ pole}$ ($R_{PP}$) of the internal geometry of the hip socket.

At the transition between the clamping cone and the ball sphere, the rounding radius ($R_{insert\ rounding}$) of the back side of the socket insert is preferably equal to the rounding radius ($R_{socket\ rounding}$) of the internal geometry of the hip socket.

One preferred embodiment is characterized in that, at the transition between the clamping cone and the ball sphere, in each case a rounding radius is present, and $R_{insert\ back\ side}$ ($R_{ER}$) is approximately the same as $R_{socket\ pole}$ ($R_{PP}$), and $R_{insert\ rounding}$ ($R_{EV}$) is larger than $R_{socket\ rounding}$ ($R_{PV}$), the socket insert is made of aluminum oxide-mixed ceramic, and the hip socket is a thin-walled metal socket.

The following approach is proposed to avoid the above-described problems and to achieve a so-called controlled back-side contact, or also a "controlled base contact":

The back-side geometry of the socket insert and the internal geometry of the hip socket are coordinated with one another in such a way that

- on a radial contour, starting from the lower cone end to the pole of the particular component, only tangential or substantially tangential transitions occur between geometric elements
- the radial contours of the associated components, starting from the lower cone end to the pole, have only identical geometric elements, wherein the dimensions do not have to be the same
- the initial gap between the components, i.e., in the unloaded state, in the region near the cone is less than or equal to the gap in the region of the pole.

The invention is explained in greater detail below with reference to three figures.

FIG. 1 shows a hip joint prosthesis 12 according to the prior art, having a modular design. The hip joint prosthesis 12 is composed of a shank 1 which is coupled to a ball head 2, and a hip socket 4 which is coupled to a socket insert 3. The shank 1 and the hip socket 4 are generally made of metal alloys, and are joined to the body by ingrowth into the femur and the pelvic bone, respectively. The shank and the hip socket are supports for the ball head 2 and the socket insert 3, respectively. The ball head 2 is rotatably supported in the spherical recess of the socket insert 3 with a degree of freedom of one.

Figure 2:
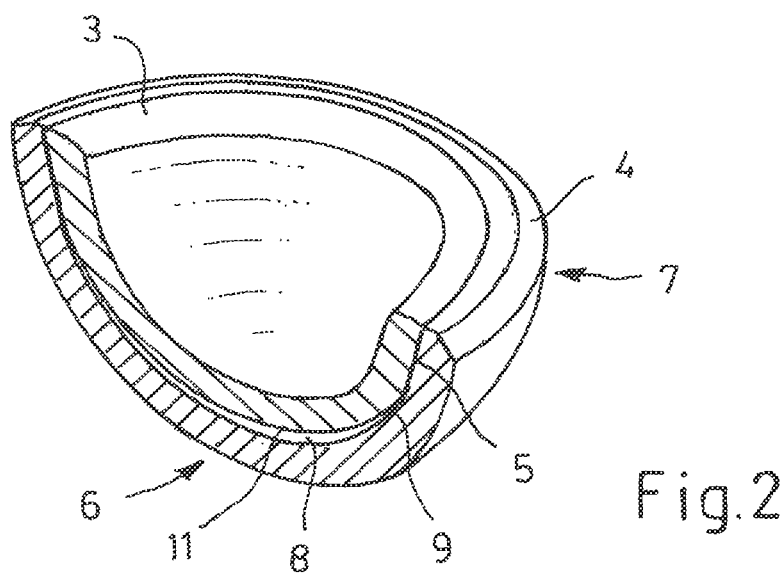
FIG. 2 illustrates a socket insert according to the present invention.
Figure 3:
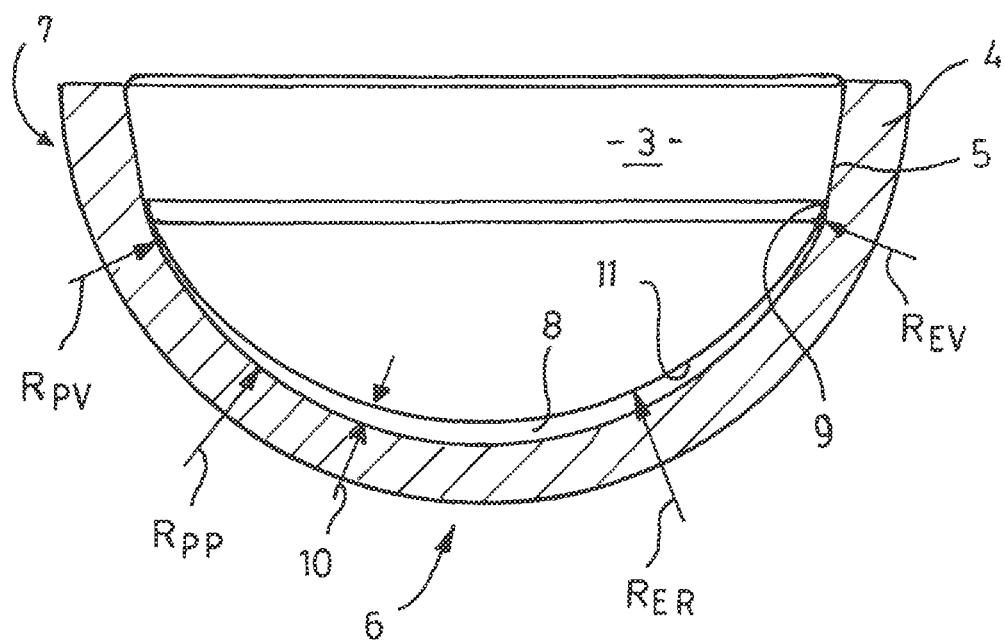
FIG. 3 illustrates a socket insert according to the present invention.

FIGS. 2 and 3 illustrate one preferred embodiment of a socket insert and a hip socket according to the invention for a hip joint prosthesis 12 (see FIG. 1). The socket insert 3 is anchored in the hip socket 4 by means of a damping cone 5. The equatorial region is denoted by reference numeral 7, and the pole is denoted by reference numeral 6. In this embodiment, the back-side geometry of the socket insert 3 and the internal geometry of the hip socket 4 are designed as ball spheres or portions of ball spheres. At the transition to the damping cone 5, in each case there is a rounding $R_{EV}$ and $R_{PV}$. The radius $R_{insert\ back\ side}$ $R_{ER}$ of the ball sphere of the back side 11 of the socket insert 3 is slightly larger than the radius $R_{socket\ pole}$ $R_{PP}$ of the internal geometry of the hip socket 4. The rounding radius $R_{insert\ rounding}$ $R_{EV}$ at the socket insert 3 is equal to the rounding radius $R_{socket\ rounding}$ $R_{PV}$ of the internal geometry of the hip socket 4. The resulting gap 8 between the components 3, 4 increases starting from region dose to the lower cone end 9 to the pole 6 of the components 3, 4. The width of the gap 8 is denoted by refence numeral 10.

It is claimed:

1. A hip joint prosthesis comprising:
   a hip socket comprising metal walls;
   a socket insert comprising a ceramic, said socket insert having a back side;
   a ball sphere; and
   a conical clamping connection;
   wherein the conical clamping connection couples the socket insert to the hip socket in an equatorial region of the socket insert and the hip socket;
   wherein in an unloaded state there is a gap between the a hip socket surface and a surface of the socket insert facing said hip socket surface; and wherein the metal walls of the hip socket are of a thickness such that when a load is applied to the socket insert the hip socket is flexible and expands, wherein the socket insert on the clamping cone may slide into an interior of the hip socket; and
   wherein at a transition between a clamping cone and the ball sphere, in each case a rounding radius is present, and $R_{insert\ back\ side}$ ($R_{ER}$) is approximately the same as $R_{socket\ pole}$ ($R_{PP}$), and $R_{insert\ rounding}$ ($R_{EV}$) is larger than $R_{socket\ rounding}$ ($R_{PV}$).

2. A hip joint prosthesis according to claim 1, wherein the width of the initial gap between the hip socket and the socket insert in the unloaded state of the socket insert in the region near the conical clamping connection is less than or equal to the width of the gap in the region of a pole thereof.

3. A hip joint prosthesis according to claim 1, wherein the width of the initial gap between the hip socket and the socket insert in the unloaded state of the socket insert continuously increases, starting from the region near the conical clamping connection to a pole thereof.

4. A hip joint prosthesis according to claim 1, wherein the ceramic comprises at least one member selected from the group consisting of aluminum oxide ceramic, zirconium oxide and silicon-nitride.

5. A hip joint prosthesis according to claim 1, wherein the ceramic is a mixed ceramic.

6. A hip joint prosthesis according to claim 5, wherein the mixed ceramic comprises at least one ceramic selected from the group consisting of aluminum oxide and silicon-nitride.

7. A hip joint prosthesis according to claim 1, wherein contact between the hip socket and the socket insert occurs in the back side.

\* \* \* \* \*